United States Patent [19]

Ward

[11] 4,051,191
[45] Sept. 27, 1977

[54] SOLID PHOSPHORIC ACID CATALYZED ALKYLATION OF AROMATIC HYDROCARBONS

[75] Inventor: Dennis J. Ward, South Barrington, Ill.

[73] Assignee: UOP Inc., Des Plaines, Ill.

[21] Appl. No.: 756,523

[22] Filed: Jan. 3, 1977

[51] Int. Cl.² .............................................. C07C 3/54
[52] U.S. Cl. .............................. 260/671 R; 260/671 P; 260/674 R
[58] Field of Search ............ 260/674 R, 671 R, 671 P

[56] References Cited
U.S. PATENT DOCUMENTS 3,499,826  3/1970  Sulzbach et al. ................ 260/671 R
3,510,534  5/1970  Sulzbach ........................ 260/671 R Primary Examiner—Delbert E. Gantz
Assistant Examiner—C. E. Spresser
Attorney, Agent, or Firm—James R. Hoatson, Jr.; John F. Spears, Jr.; William H. Page, II

[57] ABSTRACT

A process for the alkylation of aromatic hydrocarbons using a solid phosphoric acid catalyst in which liquid phosphoric acid is removed from the bottoms stream of the rectification column to which the alkylation zone effluent is charged. The acid is removed by passing the bottoms stream into a settling vessel operated at a lower pressure and temperature than the bottom of the rectification column.

2 Claims, 1 Drawing Figure

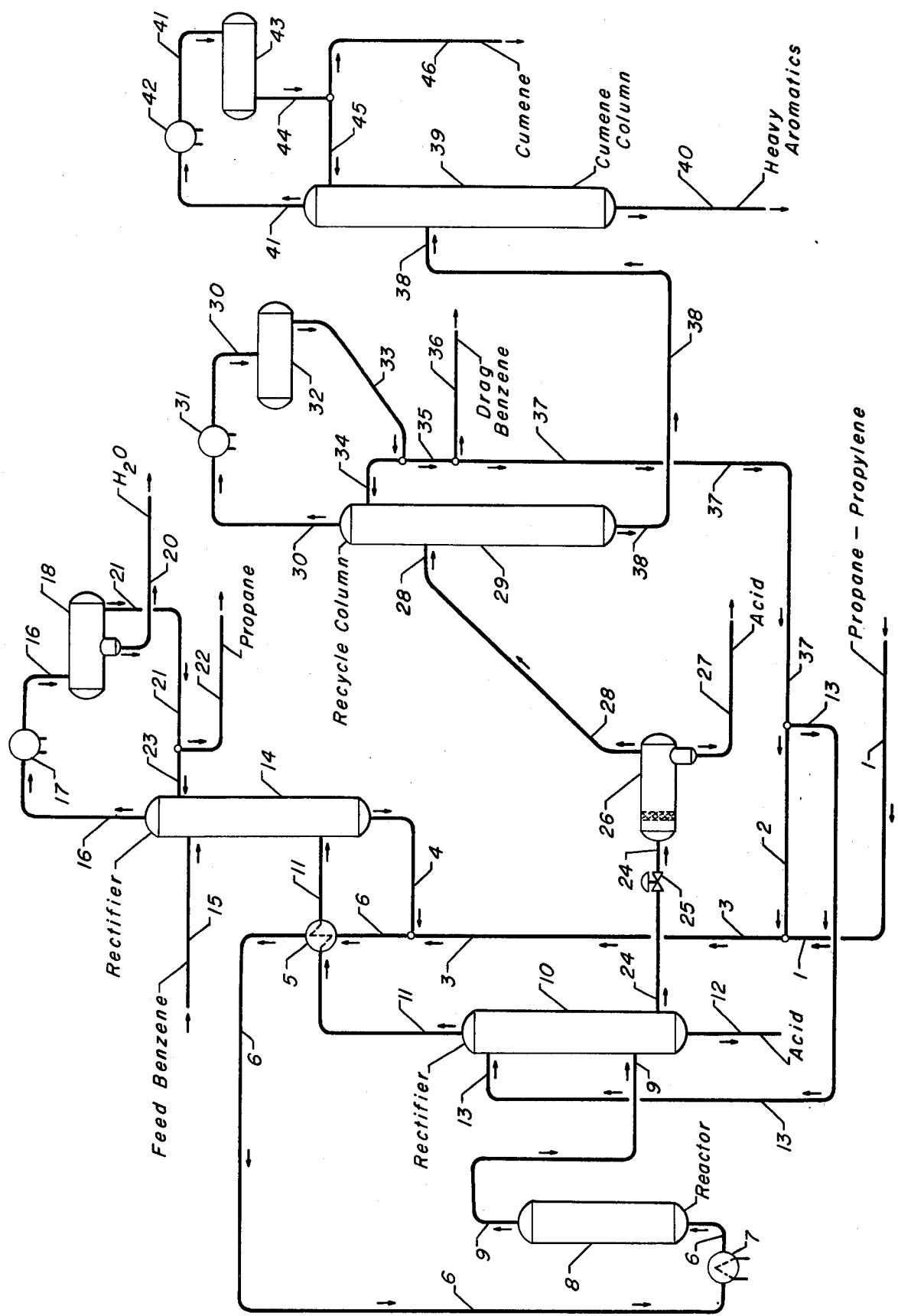

SOLID PHOSPHORIC ACID CATALYZED ALKYLATION OF AROMATIC HYDROCARBONS

FIELD OF THE INVENTION

The invention relates to a hydrocarbon conversion process. The invention more specifically relates to an improved process for the alkylation of aromatic hydrocarbons using a solid phosphoric acid catalyst. The invention also relates to a separatory method used to recover alkylaromatic hydrocarbons from the effluent of a solid phosphoric acid catalyzed alkylation process.

PRIOR ART

The alkylation of aromatic hydrocarbons using a solid phosphoric acid catalyst is a well developed art which is practiced commercially. One commercial application of the process is the alkylation of benzene with propylene to form cumene, which is used to produce phenol and acetone. Those skilled in the art are therefore familiar with the design and operation of the process.

The prior art is well described in the literature. For instance, a typical prior art flow scheme is presented as FIG. 1 of the article beginning at page 91 of the March 1976 edition of *Hydrocarbon Processing*. A portion of this flow shceme is also shown in U.S. Pat. No. 3,510,534 (Cl. 260-671). In this latter reference the utilization of SPA (solid phosphoric acid) for both the alkylation of aromatic hydrocarbons and the oligomerization of olefins is described. The process flow described in greatest detail is directed to the recovery of cumene from the effluent of a benzene alkylation zone. The effluent is passed into a first rectification column and flashed. Reflux is provided to this column by passing a portion of the recycled benzene into the top of the column. The overhead vapors of the first rectifier are passed into a second rectification column. The liquid portion of the alkylation zone effluent is separated into two liquid phases in the bottom of the first rectification column. A small amount of denser phosphoric acid is drained from the bottom of this column, and a hydrocarbon bottoms stream is removed at slightly higher elevation. This bottoms stream passes through a pressure reduction valve and into a benzene recycle column which is operated at a lower pressure than the first rectification column. Benzene is removed as the overhead product of this column and cumene is removed in the bottoms stream for recovery in a second column. It is believed that heretofore the bottoms stream of the first rectification column or its equivalent was passed directly into the downstream recycle column without the removal of phosphoric acid from the bottoms stream.

This passage of an SPA alkylation zone effluent stream into a first fractionation zone, followed by withdrawal of the product alkylated aromatic hydrocarbon in a bottoms stream which is passed into a second fractionation zone is also shown in U.S. Pat. Nos. 3,499,826 (Cl. 204-27); 3,520,944 and 3,520,945.

BRIEF SUMMARY OF THE INVENTION

The invention provides a process for the SPA catalyzed production of alkylaromatic hydrocarbons wherein corrosion in the fractionation columns utilized to recover the alkylaromatic hydrocarbons is reduced. This improvement is accomplished by depressurizing the bottoms stream of a first fractionation zone and passing the thus cooled bottoms stream into a settling vessel operated at quiescent conditions which effect the separation of liquid phase phosphoric acid from the bottoms stream. This phosphoric acid is thereby removed from the process and the amount of corrosion in the carbon steel fractionation column downstream of the settling vessel is reduced.

DESCRIPTION OF THE DRAWING

The Drawing illustrates the preferred embodiment of the invention. For clarity and simplicity various subsystems and apparatus associated with the operation of the process have not been shown. These items include flow and pressure control valves, pumps, temperature and pressure monitoring systems, reactor and fractionator internals, etc., which may be of customary design. This representation of the preferred embodiment is not intended to preclude from the scope of the invention those other embodiments set out herein or which are the result of reasonable and normal modification of these embodiments.

Referring now to the Drawing, a feed stream comprising a mixture of propane and propylene enters the process in line 1 and is admixed with a stream of recycle benzene from line 2. The resultant admixture is carried by line 3 to the junction with line 4, where it is commingled with additional benzene from line 4. This produces the alkylation zone feed stream carried by line 6. This stream is first heated in heat exchanger 5 and then in heater 7 prior to being inserted into the bottom of reactor 8. Contacting of the alkylation zone feed stream with an SPA catalyst maintained at alkylation-promoting conditions effects the reaction of at least a major portion of the propylene with benzene to form cumene or isopropylbenzene. A reaction zone effluent stream comprising benzene, propane and cumene is therefore removed in line 9.

The reaction zone effluent stream passes through a pressure control valve not shown and then into a first rectifier or rectification column 10 which is operated at a lower pressure and temperature than reactor. Vapors liberated from the reaction zone effluent stream pass upward through fractionation trays countercurrent to liquid generated by the addition of benzene from line 13 at the top of the rectifier. An overhead vapor stream comprising benzene, propane and a small amount of water is removed in line 11 and heat exchanged against the alkylation zone feed stream. It is then passed into a second rectifier 14. The bottoms stream of this column contains benzene which is passed to the reactor via line 4. A feed benzene stream enters the column through line 15 to be dried. An overhead vapor stream comprising water and propane is removed from the second rectifier in line 16 and passed through an overhead condenser 17. The resultant condensate stream is passed into overhead receiver 18 and separated into an aqueous phase removed in line 20 and a liquid propane stream removed in line 21. A net propane stream removed from the process in line 22 comprises the propane entering through line 1. The remainder of the liquid propane stream is passed into the rectifier via line 23 as reflux.

A very small amount of aqueous phosphoric acid is removed from the first rectifier in line 12. The hydrocarbonaceous bottoms stream of this column is removed in line 24 and comprises benzene and cumene. This bottoms stream is subjected to a flashing operation which lowers its pressure and temperature by passage through valve 25 into a settling vessel 26. The lower temperature and quiescent conditions maintained in the settling vessel cause a phosphoric acid phase to form in the settling vessel. This additional acid is removed in line 27 and therefore does not enter the downstream vessels.

Substantially all of the hydrocarbons in the rectifier bottoms stream continue through line 28 to a benzene recycle column 29. This column is operated at conditions which are effective to vaporize substantially all of the benzene in the rectifier bottoms stream and form an overhead vapor stream comprising benzene. This vapor stream is condensed in overhead condenser 31 and passed into overhead receiver 32 via line 30. The resultant benzene-rich liquid is removed in line 33, with a first portion delivered to the recycle column in line 34 as reflux and a second portion entering line 35. A drag stream is removed in line 36 to prevent the buildup within the process of hydrocarbons having boiling points between benzene and propane. The remainder of the benzene is passed through line 37 for recycling to the reactor and for reflux to the first rectifier.

Cumene and other alkylaromatic hydrocarbons are withdrawn from the benzene recycle column as a bottoms stream in line 38 and passed into a cumene column 39. The operation of this column is effective to cause the production of an overhead vapor stream of relatively pure cumene. This vapor stream is passed through condenser 42 into overhead receiver 43 via line 41. The cumene is withdrawn from the receiver in line 44 and divided between the reflux stream carried by line 45 and a net product stream carried by line 46. A net bottoms stream comprising polyalkylated aromatic hydrocarbons is removed from the cumene column in line 40.

DETAILED DESCRIPTION

SPA (solid phosphoric acid) catalysts find utility in a number of chemical conversion processes which are performed commercially. These processes include the oligomerization, often called polymerization, of olefins to form motor fuel, tetramer for detergent manufacture and $C_7$, $C_8$, $C_9$ and $C_{12}$ olefins for use in petrochemical processes and also the alkylation of aromatic hydrocarbons. The aromatic hydrocarbons which may be alkylated with an SPA ctalyst include benzene, toluene, xylenes, ethylbenzene, normal propylbenzene, isopropylbenzene and other cyclic compounds. Higher molecular weight and polycyclic aromatic hydrocarbons may also be alkylated using a solid phosphorus-containing catalyst. The alkylating agent may be an olefin-acting compound such as an alcohol, ether or ester including alkyl halides, alkyl sulfates and alkyl phosphates. Preferably, the alkylating agent is a mono- or di-olefin having from 2 to 8 carbon atoms per molecule. The preferred mono-olefins include ethylene, propylene, 1-butene, 2-butene and isobutylene. These olefins may be used as relatively pure streams containing a single hydrocarbon species. Alternatively, a mixture of two or more olefins or of olefins and paraffins may be used as the non-aromatic feed stream to the process. Typical products include cumene, ethylbenzene and cymene (isopropyl toluene).

The subject invention is practiced with a reaction zone containing a solid, phosphorus-containing catalyst. Preferably, the catalyst is one commonly referred to as an SPA catalyst. Suitable SPA catalysts are available commercially. As used herein the term "SPA catalyst" or its equivalent is intended to refer generically to a solid catalyst which contains as one of its principal raw ingredients an acid of phosphorus such as ortho-, pyro- or tetra-phosphoric acid. These catalysts are normally formed by mixing the acid with a siliceous solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, fullers earth and iron compounds including iron oxide have been added to the carrier to increase its strength and hardness. The combination of the carrier and the additives normally comprises about 15–30 wt.% of the catalyst, with the remainder being the phosphoric acid. However, the amount of phosphoric acid used in the manufacture of the catalyst may vary from about 8–80 wt.% of the catalyst as described in U.S. Pat. No. 3,402,130. The amount of the additive may be equal to about 3–20 wt.% of the total carrier material. Further details as to the composition and production of typical SPA catalysts may be obtained from U.S. Pat. Nos. 3,050,472; 3,050,473 and 3,132,109 and from other references.

It is known in the art that the passage of aromatic hydrocarbons through an alkylation zone tends to leach chemically combined water out of an SPA catalyst. This is acknowledged in U.S. Pat. Nos. 3,510,534 and 3,520,945, the latter of which is directed to the control of the state of hydration of the catalyst. The water content of the catalyst is important since dehydration causes the SPA catalysts to deteriorate by powdering and caking, while excess water causes the catalysts to soften and eventually form a sludge which would plug the reactor. Water is therefore injected into the feed stream to maintain the catalyst at the proper state of hydration by replacing the water leached from the catalyst. The rate of this injection is used to control the catalyst hydration level, and the feed streams are therefore maintained as dry as practical prior to the water injection point. This results in the total water content of the feed being essentially the same as the amount injected. Typical water injection rates are from about 100 ppm. to 2000 ppm. in aromatic hydrocarbon alkylation operations. A preferred water addition rate during the production of cumene is from about 200 to 300 ppm. of the combined feed to the reaction zone.

The water which has been leached from the catalyst and the excess water added to the feed stream are contained in the reaction zone effluent stream. This water contains phosphorus from the catalyst and is therefore phosphoric acid of some varying strength. The acid is present at very low concentrations in the reaction zone effluent and is apparently dissolved in the much larger aromatic hydrocarbon stream. However, the reaction zone effluent is normally cooled as by flashing, and at the resultant lower temperature a separate aqueous phase of phosphoric acid is formed. Experience has shown that the hot reaction zone effluent material is not corrosive, but that the cooler, two liquid phase effluent material is fairly corrosive to carbon steel. For this reason at least the lines and vessels immediately downstream of the reaction zone are normally made of stainless steel. The acid therefore collects in the bottom of the first vessel, which in a process flow similar to that shown in the Drawing is the first rectification column. It is for this reason that the previously cited patents show acid being withdrawn from the first fractionation column into which the reaction zone effluent is charged. This first fractionation column is normally a rectifier and is normally used in conjunction with either a second rectifier, an absorber or a depropanizer. This first fractionation column and any other column associated with it are referred to herein as the first fractionation zone.

A bottoms stream containing the alkylaromatic hydrocarbon product of the process is normally removed from the first fractionation zone and passed into a second fractionation zone. Since this bottoms stream often contains benzene it is a common practice to first remove the benzene and other hydrocarbons boiling below cumene in a first column referred to as a benzene recycle column. The cumene or other alkylaromatic hydrocarbon product is then recovered in a second column referred to as a cumene column. Differing column arrangements may be utilized to perform the product recovery. These columns are referred to herein as the second fractionation zone.

The benzene recycle column is typically operated at a lower pressure and temperature than the column producing the bottoms stream which is fed to it. In the prior art the bottoms stream of the first fractionation column is flashed into the benzene recycle column, and is therefore cooled to a lower temperature. This lower temperature causes another small amount of the phosphoric acid to drop out of solution in the benzene recycle column. To avoid the high cost of stainless steel, the benzene recycle column is often made of carbon steel. The phosphoric acid therefore corrodes the fractionation trays located in this column. This slowly reduces the efficiency of the corroding trays, and may reduce the efficiency of other trays by causing the accumulation of corrosion products or debris on the surface of the trays. It is an objective of this invention to provide a method of reducing the amount of corrosion such as this by lowering the amount of phosphoric acid which is passed into the benzene recycle column.

According to the inventive concept the alkylaromatic hydrocarbon-containing bottoms stream of the first fractionation zone is flashed to a lower pressure at a point prior to the second fractionation zone. The liquid phase material remaining after the flashing operation is then retained for some time in a quiescent settling zone which is maintained at conditions which allow phosphoric acid to settle out by gravity and to be decanted. This settling operation may be aided by the provision of a coalescing means of either a mechanical or electrostatic type. The preferred type of settling zone is a settling vessel similar to that depicted in the drawing and which is commonly used as for overhead receivers. Other types of vessels, including those having separate facilities for handling the vapor phase formed by the flashing operation may be used.

The flashing operation performed prior to the settling vessel preferably reduces the pressure of the bottoms stream to the lowest pressure which still provides an adequate pressure differential between the settling vessel and the second fractionation zone to transfer the bottoms stream to the second fractionation zone without the use of a pump. A lower pressure and temperature may be used however if suitable pumping means are supplied. The flashing operation preferably reduces the temperature of the bottoms stream by 80° F. or more. No control system need be used to regulate the hydrocarbon flow from the settling vessel, and it may be directly coupled to the second fractionation zone. In the preferred embodiment the pressure in the settling vessel is higher than that in the second fractionation zone only by the pressure drop associated with the flow of the bottoms stream through the connecting lines and any elevation differential.

The conditions of temperature and pressure maintained in the first fractionation zone and also in the second fractionation zone are interrelated and variable. The first fractionation zone is preferably operated at a pressure at least 100 psig. higher than the second fractionation zone and at a temperature over about 100° F. above that used in the second fractionation zone. A broad range of conditions for the first fractionation zone include a bottoms temperature of about 350° F. to 500° F. and a top pressure of about 300 to about 600 psig. or higher. A broad range of conditions for use in the second fractionation zone includes a top pressure of about 10 to 150 psig. and a bottoms temperature of about 300° to 450° F.

The reaction zone is maintained at alkylation-promoting conditions which include a pressure of about 300 to 1000 psig. and a temperature of about 300° to 600° F. The liquid hourly space velocity of reactants may range from about 0.5 to 2.5. It is preferred that an excess of the aromatic hydrocarbon be present in the reaction zone. The mole ratio of the aromatic hydrocarbon to the olefin should be within the broad range of 3:1 to 20:1. A ratio of about 8:1 is preferred for the production of cumene. It is preferred that the reactant stream be mixed-phase through the reactor. The feed stream therefore preferably contains some unreactive light paraffins having the same number of carbon atoms per molecule as the olefin. In the production of cumene it is preferred that the amount of propane in the reaction zone feed stream be at least equal to the amount of propylene in this stream. This may be accomplished by using a dilute propylene feed stream or by recycling propane.

The invention may be further illustrated by this example of the preferred embodiment based on the production of cumene by the alkylation of benzene with propylene. For clarity, reference will be made to lines and vessels shown in the Drawing. The feed stream to the reaction zone is derived from a bottoms stream of rectifier 14 which comprises about 4,890 mph (moles per hour), of which about 67 mol.% is benzene and 26 mol.% is propane and a recycle stream from line 2 comprising about 2,980 mph of benzene and some propane. About 133 lb/hr. of water is injected into this mixture to maintain the proper state of hydration of the catalyst. The propylene feed stream enters the process at the rate of about 852 mph. The combined feed stream contains about 9,195 mph of which 6275 mph is benzene. It is split into two identical streams, each of which is passed into the bottom of a reactor at a pressure of about 550 psig. and a temperature of about 383° F. The reactors each contain four catalyst beds of sufficient overall volume to provide a WHSV of about 1.25 hr.$^{-1}$. The catalyst used is a standard SPA catalyst.

The mixed-phase effluents of the two reactors are cooled from about 437° F. to about 395° F. by being lowered in pressure from about 500 psig. to about 271 psig. and are then combined. The resultant alkylation zone effluent enters the first rectifier 10 at a rate of about 8419 mph. Also fed to the first rectifier is a 519 mph benzene-rich stream from line 13 at a temperature of about 120° F. The first rectifier is operated with a bottom temperature of 394° F. at 271 psig. The overhead vapor stream is removed at a temperature of approximately 379° F. and cooled to about 310° F. in heat exchanger 5 before being passed into the second rectifier. The first rectifier contains eight fractionation trays and the second rectifier contains 28 fractionation trays. A very small acid stream of about 1 gal/day is removed from the bottom of the rectifier.

The benzene feed stream enters the second rectifier at the eighteenth tray from the bottom at about 746 mph and at a temperature of approximately 80° F. The overhead vapor of this column has a temperature of about 123° F. and is cooled to about 100° F. in the overhead condenser. The overhead receiver is maintained at 250 psig. About 7 mph of water and 57.7 mph of liquid hydrocarbons are removed from the receiver. About 92 mol.% of this stream is propane with the rest being ethane, isobutane and hydrogen. The reflux stream has a flow rate of about 2,482 mph. A stabbed-in reboiler is used in the second rectifier to provide a 251° F. bottoms stream.

The net bottoms stream is flashed from approximately 394° F. and 271 psig. to about 50 psig. and passed into the settling vessel 26 as a two phase stream having a temperature of about 291° F. This temperature reduction causes an additional small amount of phosphoric acid to come out of solution in the hydrocarbon stream. It is removed from the vessel at a rate of less than 1 gal/day. The bottoms stream of the first rectifier is then passed into a 36-tray recycle column. This column is operated with a bottoms temperature of about 418° F. A largely benzene overhead vapor stream is removed at about 40 psig. and condensed at a temperature of 120° F. The overhead liquid is divided between reflux and a recycle stream. A drag stream of about 4 mph is withdrawn to remove unreactive hydrocarbons, and the remainder of the recycle stream forms the previously specified rectifier reflux and reactor feed streams.

A 750 mph bottoms stream of the recycle column is passed into the 45-tray cumene column. The overhead vapor stream of this column has a pressure of approximately 20 psig. at a temperature of about 374° F. It is condensed to form reflux and a 716 mph net cumene product stream. The cumene column is operated with a bottoms temperature of about 478° F., and a net bottoms stream of impurities is removed at the rate of about 33.6 mph.

I claim as my invention:

1. In the process for the production of alkylaromatic hydrocarbons wherein an aromatic hydrocarbon and an olefin are contacted with a solid phosphoric acid-containing catalyst in a reaction zone maintained at alkylation-promoting conditions; a reaction zone effluent stream comprising the aromatic hydrocarbon and an alkylaromatic hydrocarbon are passed into a first fractionation zone; a bottoms stream comprising the aromatic hydrocarbon and the alkylaromatic is removed from the first fractionation zone at a first temperature and then passed into a second fractionation zone at a lower pressure and at a lower second temperature; the improvement which comprises flashing the bottoms stream at an intermediate point between the first fractionation zone and the second fractionation zone and then passing the bottoms stream into a settling vessel and removing released phosphoric acid from the settling vessel to thereby reduce the amount of phosphoric acid which enters the second fractionation zone.

2. The improvement of claim 1 wherein the aromatic hydrocarbon is benzene and the olefin has from 2 to 3 carbon atoms per molecule.

* * * * *